(12) United States Patent
Niimoto et al.

(10) Patent No.: US 7,592,485 B2
(45) Date of Patent: Sep. 22, 2009

(54) PROCESS FOR PRODUCING (Z)-1-PHENYL-1-DIETHYLAMINO CARBONYL-2-AMINOMETHYL CYCLOPROPANE HYDROCHLORIDE

(75) Inventors: Yoshihide Niimoto, Kobe (JP); Hiroharu Kumazawa, Takatsuki (JP); Osamu Tokuda, Nara (JP); Fumiaki Ibukuro, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 178 days.

(21) Appl. No.: 11/630,253

(22) PCT Filed: Jun. 23, 2005

(86) PCT No.: PCT/JP2005/012011

§ 371 (c)(1),
(2), (4) Date: Dec. 21, 2006

(87) PCT Pub. No.: WO2006/001493

PCT Pub. Date: Jan. 5, 2006

(65) Prior Publication Data

US 2008/0051604 A1  Feb. 28, 2008

(30) Foreign Application Priority Data

Jun. 24, 2004  (JP) ............................. 2004-186982

(51) Int. Cl.
*C07C 231/12* (2006.01)

(52) U.S. Cl. .................................................... 564/164
(58) Field of Classification Search ................. 564/164
See application file for complete search history.

(56) References Cited

FOREIGN PATENT DOCUMENTS

| AU | B-56343/86 | 10/1986 |
| EP | 0200638 A * | 4/1986 |
| JP | 61-251650 | 11/1986 |

OTHER PUBLICATIONS

Bonnaud, Bernard et al., "1-Aryl-2-(aminomethyl)cyclopropanecarboxylic Acid Derivatives. A New Series of Potential Antidepressants", J. Med. Chem., 1987, vol. 30, pp. 318-325.
Kennewell, Peter D. et al., Synthesis of y-Aminobutyric Acid Analogues of Restricted Conformation. Part 2.¹ The 2-(Aminomethyl) cycloalkanecarboxylic Acid †, J. Chem. Soc. Perkin Trans. I, 1982, No. 11, pp. 2563-2570.

* cited by examiner

*Primary Examiner*—Peter G O'Sullivan
(74) *Attorney, Agent, or Firm*—Foley & Lardner LLP

(57) ABSTRACT

The present invention provides a process for producing (Z)-1-phenyl-1-diethylaminocarbonyl-2-aminomethylcyclopropane or hydrochloride thereof, which comprises a step of reacting (Z)-1-phenyl-1-diethylaminocarbonyl-2-phthalimidomethylcyclopropane by contacting said compound with an aqueous methylamine solution having a concentration of from 1 to 25% by weight to obtain (Z)-1-phenyl-1-diethylaminocarbonyl-2-aminomethylcyclopropane.

8 Claims, No Drawings

PROCESS FOR PRODUCING (Z)-1-PHENYL-1-DIETHYLAMINOCARBONYL-2-AMINOMETHYLCYCLOPROPANE HYDROCHLORIDE

FIELD OF THE INVENTION

The present invention relates to a process for producing (Z)-1-phenyl-1-diethylaminocarbonyl-2-aminomethylcyclopropane hydrochloride useful as an antidepressant.

BACKGROUND OF THE INVENTION (Z)-1-Phenyl-1-diethylaminocarbonyl-2-aminomethylcyclopropane hydrochloride is known as an antidepressant having and activity of serotonin-noradrenalin reuptake inhibitor.

As one of most effective methods for producing (Z)-1-phenyl-1-diethylaminocarbonyl-2-aminomethylcyclopropane hydrochloride, disclosed is a process represented by the following scheme wherein (Z)-1-phenyl-1-diethylaminocarbonyl-2-phthalimidomethylcyclopropane is treated by 40% aqueous solution of methylamine to deprotect the phthalimide group and then converted to a hydrochloride thereof by an ethanol solution of hydrogen chloride (refer to EP0200638A).

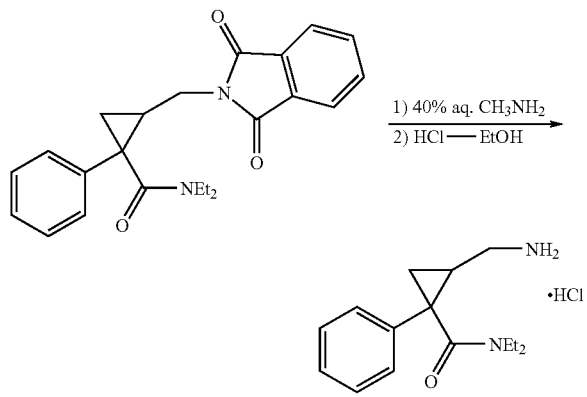

The above-mentioned process has problems that, when (Z)-1-phenyl-1-diethylaminocarbonyl-2-phthalimidomethylcyclopropane is treated by 40% aqueous solution of methylamine, by-produced N,N'-dimethylphthalamide precipitates out in a reactant mixture forming a dispersed state, thereby disturbing smooth extraction processing.

Furthermore, the process applies an ethanol solution of hydrogen chloride in the step to obtain hydrochloride salt; but since ethanol has too high solubility for (Z)-1-phenyl-1-diethylaminocarbonyl-2-aminomethylcyclopropane hydrochloride, the solubility must be controlled by adding ethers such as diethyl ether or diisopropyl ether. However, addition of ethers having high ignitability causes problems of safety in industrial applications.

SUMMARY OF THE INVENTION

The present invention intends to solve the above problems and to provide a simple and safe process for producing (Z)-1-phenyl-1-diethylaminocarbonyl-2-aminomethylcyclopropane hydrochloride with high quality and yield.

After having diligently studied to solve the above problems, the present inventors have achieved the present invention.

Namely, the invention has the following aspects.

<1> A process for producing (Z)-1-phenyl-1-diethylaminocarbonyl-2-aminomethylcyclopropane or hydrochloride thereof, which comprises a step of reacting (Z)-1-phenyl-1-diethylaminocarbonyl-2-phthalimidomethylcyclopropane by contacting said compound with an aqueous methylamine solution having a concentration of from 1 to 25% by weight to obtain (Z)-1-phenyl-1-diethylaminocarbonyl-2-aminomethylcyclopropane.

<2> The process according to <1>, wherein the concentration of the aqueous methylamine solution is from 10 to 25% by weight.

<3> The process according to <1> or <2>, wherein the amount of methylamine is 4 to 20 gram equivalent per one gram equivalent of (Z)-1-phenyl-1-diethylaminocarbonyl-2-phthalimidomethylcyclopropane.

<4> The process according to any of <1> to <3>, wherein the contact is carried out in the co-presence of an organic solvent.

<5> The process according to <4>, wherein the organic solvent is the one comprising toluene.

<6> The process according to <4>, wherein the organic solvent is the one consisting essentially of toluene.

<7> The process according to any of <1> to <6>, which further comprises a step contacting (Z)-1-phenyl-1-diethylaminocarbonyl-2-aminomethylcyclopropane with hydrogen chloride in an organic solvent comprising ethyl acetate and isopropyl alcohol.

<8> The process according to <7>, wherein the organic solvent is the one consisting essentially of ethyl acetate and isopropyl alcohol.

<9> The process according to <7>, wherein weight ratio of ethyl acetate to isopropyl alcohol is 3-20 to 1.

<10> The process according to <8>, wherein weight ratio of ethyl acetate to isopropyl alcohol is 3-20 to 1.

DESCRIPTION OF PREFERRED EMBODIMENTS

The present invention is explained in detail as follows.

The present invention is a process for producing (Z)-1-phenyl-1-diethylaminocarbonyl-2-aminomethylcyclopropane or hydrochloride thereof wherein the process includes a step of contacting (Z)-1-phenyl-1-diethylaminocarbonyl-2-phthalimidomethylcyclopropane by contacting said compound with an aqueous solution of methylamine having a concentration of 25% by weight or less, and is also a process for producing (Z)-1-phenyl-1-diethylaminocarbonyl-2-aminomethylcyclopropane hydrochloride wherein the process, succeeding to the step mentioned above, further includes a step of contacting (Z)-1-phenyl-1-diethylaminocarbonyl-2-aminomethylcyclopropane obtained with hydrogen chloride in a solvent.

(Z)-1-Phenyl-1-diethylaminocarbonyl-2-phthalimidomethylcyclopropane, which is a raw material in the present invention, is the known compound and can be produced, for example, by a process described in EP0200638A.

It is essentially necessary for the process of the present invention to set a concentration of the aqueous solution of methylamine in the range of 1 to 25% by weight, i.e. lower than 40% by weight applied in the conventional art, and preferably 10 to 25% by weight, and more preferably 14 to 25% by weight.

If the concentration of the aqueous solution of methylamine is higher then 25% by weight, by-produced N,N'- dimethylphthalamide could precipitate in a reaction system with causing a dispersed state and hindering smooth extraction operation. If the concentration is lower than 1% by weight, the reaction becomes unpractical because the reaction rate is significantly reduced.

The concentration of the aqueous solution of methylamine may easily be controlled by adding water in an on-going reaction system applied with a commercially available aqueous solution of the methylamine having 40% by weight.

The amount of methylamine contained in the aqueous solution of methylamine is necessary at least 2 gram equivalent or more per 1 gram equivalent of (Z)-1-phenyl-1-diethylaminocarbonyl-2-phthalimidomethylcyclopropane, in view of reaction rate and volume efficiency, preferably 4 to 20 gram equivalent, and more preferably 6 to 12 gram equivalent. Therefore, the aqueous solution of methylamine having the above-mentioned concentration may be used in an amount to make the amount of the methylamine substantially contained in the reaction system within the above-mentioned equivalent ranges.

The reaction of the present invention may be carried out solely in the aqueous solution of methylamine, and may also be carried out in the co-presence of an organic solvent. From the practical point of view, it is preferably carried out in the co-presence of the organic solvent used for extraction operation after the reaction. The organic solvent is preferably the one immiscible with water and un-reacted with methylamine. Examples thereof include aromatic hydrocarbon solvents such as toluene, and the like; halogenated-aromatic hydrocarbon solvents such as monochlorobenzene, dichlorobenzene, and the like; saturated hydrocarbon solvents such as hexane, heptane, and the like. These may be used alone or as a mixture of two or more kinds thereof.

When the reaction is carried out in the co-presence of an organic solvent, the ratio of the organic solvent to the aqueous solution of methylamine, under consideration of productivity (volume efficiency), is preferably 0.5 to 5 in terms of a weight ratio of organic solvent/aqueous solution of methylamine, and preferably 1 to 2.

The reaction temperature is usually 0 to 100° C., and preferably 10 to 100° C. The reaction time is usually 2 to 30 hours.

Since by-produced N,N'-dimethylphthalamide is present under dissolved condition in a water layer after the completion of the reaction, when the reaction is conducted in the co-presence of an organic solvent, N,N'-dimethylphthalamide may easily be removed by leaving the reactant mixture settled as itself and then removing a water layer by a phase separating operation. When an organic solvent is not used in the reaction, the reactant mixture may preferably extracted with the organic solvent and left settled, and then the resulting water layer is subjected to phase separation. Since (Z)-1-phenyl-1-diethylaminocarbonyl-2-aminomethylcyclopropane is dissolved in the organic layer, (Z)-1-phenyl-1-diethylaminocarbonyl-2-aminomethylcyclopropane may be isolated, if necessary, by washing with water, drying, and concentrating.

Thus, obtained (Z)-1-phenyl-1-diethylaminocarbonyl-2-aminomethylcyclopropane may be converted to a hydrochloride thereof by contacting said compound with hydrogen chloride in an organic solvent including ethyl acetate and isopropyl alcohol. As the organic solvent, an organic solvent consisting essentially of ethyl acetate and isopropyl alcohol is usually used.

The ratio of ethyl acetate to isopropyl alcohol in the organic solvent, in view of the recovery rate of the intended compound and of the quality of the obtained crystals, is preferably 3 to 20 in terms of ethyl acetate/isopropyl alcohol (weight ratio), and more preferably 5 to 10.

From the view point of operability of suspension containing crystals of the intended compound and a yield thereof, the amount of the solvent in terms of the total amount of ethyl acetate and isopropyl alcohol is preferably 2 to 10 kg per 1 kg of (Z)-1-phenyl-1-diethylaminocarbonyl-2-phthalimidomethylcyclopropane, more preferably 3 to 7 kg.

The form of hydrogen chloride to be used is not limited, and hydrogen chloride may be contacted with (Z)-1-phenyl-1-diethylaminocarbonyl-2-phthalimidomethylcyclopropane by being introduced in a gas state or being added as a solution dissolved in the solvent used in the reaction. It is preferred that hydrogen chloride is used as a solution of ethyl acetate, particularly 4 normal solution thereof because of easiness of commercial availability, easiness for quantification, and good operability.

When being used as a solution of ethyl acetate, ethyl acetate contained in the solution is counted as a part of ethyl acetate used in the reaction solvent.

The amount of hydrogen chloride, in view of the yield of the intended compound, is preferably 1 to 2 gram equivalent per 1 equivalent of (Z)-1-phenyl-1-diethylaminocarbonyl-2-phthalimidomethylcyclopropane, and more preferably 1.1 to 1.3 gram equivalent.

(Z)-1-Phenyl-1-diethylaminocarbonyl-2-aminomethylcyclopropane hydrochloride can be precipitated by contacting with hydrogen chloride, and crystals of (Z)-1-phenyl-1-diethylaminocarbonyl-2-aminomethylcyclopropane hydrochloride can be isolated by collection of crystals with filtration after stirred preferably at room temperature for 1 to 3 hours, preferably further by washing with ethyl acetate followed by drying.

The present invention will be explained in more detail according to Examples. The present invention should not be limited thereto.

REFERENTIAL EXAMPLE 1

Production of 2-oxo-1-phenyl-3-oxabicyclo{3.1.0} hexane

In a mixed solution of toluene (26.0 kg) and N,N'-dimethylimidazolidinone (94.9 kg), 60% sodium hydride (27.2 kg; 683 mol) was added, and phenylacetonitrile (40.2 kg, 343 mol) was subsequently added dropwise thereto at 10 to 20° C. After the resulting mixture was stirred for 2 hours, a mixture of epichlorohydrin (31.7 kg, 343 mol) and toluene (26.0 kg) was added dropwise thereto at 10 to 20° C. and then stirred. After confirming the disappearance of the raw material, methanol (22.0 kg) and water (120.6 kg) were added therein to be subjected to washing and phase separation.

24% Aqueous solution of potassium hydroxide (159.1 kg) and tetrabutylammonium sulfate (1.1 kg) was added to the organic layer obtained, and the mixture was heated and refluxed. After cooling down, the organic phase was removed by a phase separation. Toluene (69.6 kg) and 35% hydrochloric acid (78.7 kg) were further added to the aqueous phase, and then the mixture was stirred at 60 to 70° C. for 2 hours. After cooling down the mixture and subjecting to a phase separation, an organic layer was further washed twice with 8% aqueous sodium hydrogen carbonate solution and twice with water. The organic layer obtained was concentrated under a reduced pressure to obtain 40.7 kg of the titled compound in a form of light-yellow oily substance. Yield was 68.1%.

The obtained oily substance of 2-oxo-1-phenyl-3-oxabicyclo{3.1.0}hexane was cooled to transform crystals.

REFERENTIAL EXAMPLE 2

Production of (Z)-1-phenyl-1-diethylaminocarbonyl-2-hydroxymethylcyclopropane

After cooling a mixed solution of diethylamine (8.1 kg, 111 mol) and tetrahydrofuran (33.2 kg) down to −75° C., 17% n-butyllithium-hexane solution (40.4 kg, 108 mol) was added dropwise into the above mixture and then stirred for 1 hour. Thereafter, a solution of 2-oxo-1-phenyl-3-oxabicyclo[3.1.0]hexane(12.4 kg, 71.2 mol) dissolved with tetrahydrofuran (10.4 kg) added dropwise into the mixture and then the resulting mixture was stirred at −60 to −78° C. After completion of the reaction, the reacted liquid was added dropwise into 20% aqueous solution of ammonium chloride (43.2 kg). After subjecting to phase separation, the organic layer was concentrated by about 40% by weight under a reduced pressure. Toluene (43.1 kg) was added to the concentrated residue, and then the added mixture was washed twice with water. The organic layer obtained was concentrated under a reduced pressure to obtain 11.5 kg of light-yellow oily substance as the titled compound. Yield is 66.8%.

The obtained oily substance of (Z)-1-phenyl-1-diethylaminocarbonyl-2-hydroxymethylcyclopropane was crystallized with a mixed solvent of ethyl acetate and n-heptane to obtain light yellow crystals.

REFERENTIAL EXAMPLE 3

Production of (Z)-1-phenyl-1-diethylaminocarbonyl-2-chloromethylcyclopropane

After dissolving (Z)-1-phenyl-1-diethylaminocarbonyl-2-hydroxymethylcyclopropane (19.5 kg, 78.8 mol) with chloroform (68.9 kg), thionyl chloride (10.3 kg, 86.6 mol) was added dropwise to the above solution at 10 to 20° C. and then the mixture was stirred for 2 hours. After finishing the reaction, toluene (50.6 kg) was added thereto and then the added mixture was concentrated under a reduced pressure. After toluene (67.6 kg) was added to the concentrated residue, the resulting mixture was washed once with water, once with 8% aqueous sodium hydrogen carbonate solution and further once with water. The obtained organic layer was concentrated under a reduced pressure to obtain 20.6 kg of the titled compound in a form of light-yellow oily substance. Yield was 96.7%.

REFERENTIAL EXAMPLE 4

Production of (Z)-1-phenyl-1-diethylaminocarbonyl-2-phthalimidomethylcyclopropane After heating a mixture of potassium phthalimide (16.7 kg, 90.2 mol) and N,N-dimethylformamide (81.4 kg) up to at 50° C., a solution of (Z)-1-phenyl-1-diethylaminocarbonyl-2-chloromethylcyclopropane (19.1 kg, 71.9 mol) dissolved with N,N-dimethylformamide (9.0 kg) was added dropwise to the above mixture and then the added mixture was stirred for 2 hours. After cooling down to 20° C., seed crystals of (Z)-1-phenyl-1-diethylaminocarbonyl-2-phthalimidomethylcyclopropane was seeded into the resulting mixture, and then the inoculated mixture was stirred for 2 hours; further added dropwise with water (57.4 kg), stirred for 1 hour, and then filtered to collect crystals. The crystals were washed with water (50.0 kg), and then dried to obtain 25.0 kg of the titled compound in a form of white crystals. Yield was 92.3%.

EXAMPLE 1

Production of (Z)-1-phenyl-1-diethylaminocarbonyl-2-aminomethylcyclopropane hydrochloride (substantial concentration of aqueous methylamine solution: 21% by weight)

Into a mixture of (Z)-1-phenyl-1-diethylaminocarbonyl-2-phthalimidomethylcyclopropane (18.2 kg, 48.4 mol), water (35.0 kg), and toluene (79.0 kg), 40% by weight aqueous monomethylamine solution (37.7 kg, 485 mol; the concentration of the solution finally resulted in 21% by weight aqueous monomethylamine solution by combining the amount of the water mentioned above) was added dropwise and stirred at 20° C. for 20 hours. After phase-separating the resultant reaction mixture, a water layer was extracted twice with toluene. The organic layers obtained were mixed and dried with anhydrous magnesium sulfate, and then filtrated and concentrated under a reduced pressure. To the solution of concentrated residue added with ethyl acetate (67.1 kg) and isopropyl alcohol (9.0 kg), 4N-hydrogen chloride-ethyl acetate (12.5 kg, 55.9 mol) was added dropwise. Crystals obtained were collected by filtration, then washed with ethyl acetate, and dried to obtain white powders of (Z)-1-phenyl-1-diethylaminocarbonyl-2-aminomethylcyclopropane hydrochloride (11.9 kg).

Yield was 86.9%.

Physical Properties: 1H-NMR (D$_2$O, 400 MHz)δ:0.87(3H, t, J=7.0Hz),1.08(3H, t ,J=7.0Hz), 1.72-1.84 (3H, m), 2.43 (1H, m), 3.25-3.44(4H, m),3.71 (1H, m), 7.13-7.28 (5H, m), 8.80 (3H, br-s)

EXAMPLE 2

Production of (Z)-1-phenyl-1-diethylaminocarbonyl-2-aminomethylcyclopropane hydrochloride (substantial concentration of the aqueous methylamine solution; 15% by weight)

Into a mixture of (Z)-1-phenyl-1-diethylaminocarbonyl-2-phthalimidomethylcyclopropane (3 g, 0.008 mol), toluene (15 ml), and water (10.3 g), 40% by weight aqueous monomethylamine solution (6.20 g, 0.080 mol; the concentration of the solution finally resulted in 15% by weight aqueous monomethylamine solution by combining the amount of the water mentioned above) was added dropwise and stirred at 20° C. for 18 hours; yield determined with high-performance liquid chromatography (hereinafter, referred to as LC quantified value) was 92.1%, and un-reacted raw material was remained.

EXAMPLE 3

Production of (Z)-1-phenyl-1-diethylaminocarbonyl-2-aminomethylcyclopropane hydrochloride (substantial concentration of the aqueous methylamine solution: 10% by weight)

The experiment was carried out in the same manner as in Example 2 except that the amount of water was 18.6 g. The LC quantified value was 88.0%, un-reacted raw material was remained, and the reaction rate tended to delay in comparison with that of Example 2.

EXAMPLE 4

Production of (Z)-1-phenyl-1-diethylaminocarbonyl-2-aminomethylcyclopropane hydrochloride (substantial concentration of the aqueous methylamine solution: 14.5% by weight)

Into a mixture of (Z)-1-phenyl-1-diethylaminocarbonyl-2-phthalimidomethylcyclopropane (16.7 kg, 44.4 mol), water (36.1 kg), and toluene (72.3 kg), 40% by weight aqueous methylamine solution (20.7 kg, 266 mol; the concentration of the solution finally resulted in 14.5% by weight aqueous methylamine solution by combining the amount of the water mentioned above) was added dropwise and stirred at 40° C. for 4 hours. After phase-separating the resultant reaction mixture, a water layer was extracted twice with toluene. The organic layers obtained were mixed and dried with anhydrous magnesium sulfate, and then filtrated and concentrated under a reduced pressure. To the solution of concentrated residue added with ethyl acetate (64.0 kg) and isopropyl alcohol (8.5 kg), 4N-hydrogen chloride-ethyl acetate (11.0 kg, 46.2 mol) was added dropwise. Crystals obtained were collected by filtration, then washed with ethyl acetate, and dried to obtain white powders of (Z)-1-phenyl-1-diethylaminocarbonyl-2-aminomethylcyclopropane hydrochloride (10.9 kg).

Yield was 88.2%.

COMPARATIVE EXAMPLE 1

Production of (Z)-1-phenyl-1-diethylaminocarbonyl-2-aminomethylcyclopropane hydrochloride (substantial concentration of the aqueous methylamine solution; 40% by weight)

The experiment was carried out in the same manner as in Example 2 except that no water was added; 18 hours was required until the raw material nearly disappeared. The reaction system was thick at the beginning, and left in a slurry state until the end of reaction.

COMPARATIVE EXAMPLE 2

Production of (Z)-1-phenyl-1-diethylaminocarbonyl-2-aminomethylcyclopropane hydrochloride (substantial concentration of the aqueous methylamine solution: 27% by weight)

The experiment was carried out in the same manner as in Example 2 except that water was used in an amount of 3 g. The reaction proceeded as nearly same as in Comparative Example 1, and the reaction system was left in a slurry state by the end of reaction.

The process of the present invention allows to remove by-produced N,N'-dimethylphthalamide with a simple operation such as phase separation of water layer, thereby has advantages compared to the conventional processes which require troublesome procedures such as extraction from a suspension.

Furthermore, in the process of the present invention, using a mixed solvent of ethyl acetate and isopropyl alcohol in the step of converting (Z)-1-phenyl-1-diethylaminocarbonyl-2-aminomethylcyclopropane to a hydrochloride thereof allows to obtain (Z)-1-phenyl-1-diethylaminocarbonyl-2-aminomethylcyclopropane hydrochloride in high quality and high yield, thereby the process of the invention is more highly practical than the conventional process which requires unsafe solvent such as ether or the like.

The invention claimed is:

1. A process for producing (Z)-1-phenyl-1-diethylaminocarbonyl-2-aminomethylcyclopropane hydrochloride which comprises a step of reacting (Z)-1-phenyl-1-diethylaminocarbonyl-2-phthalimidomethylcyclopropane in the presence of an organic solvent comprising toluene by contacting said compound with an aqueous methylamine solution having a concentration of from 1 to 25% by weight to obtain (Z)-1-phenyl-1-diethylaminocarbonyl-2-aminomethylcyclopropane and a step of contacting (Z)-1-phenyl-1-diethylaminocarbonyl-2-aminomethylcyclopropane with hydrogen chloride in an organic solvent comprising ethyl acetate and isopropyl alcohol.

2. The process according to claim 1, wherein the organic solvent is the one consisting essentially of ethyl acetate and isopropyl alcohol.

3. The process according to claim 1, wherein weight ratio of ethyl acetate to isopropyl alcohol is 3-20 to 1.

4. The process according to claim 2, wherein weight ratio of ethyl acetate to isopropyl alcohol is 3-20 to 1.

5. The process according to claim 1, wherein the amount of hydrogen chloride is 1 to 2 gram equivalent per 1 gram equivalent of (Z)-1-phenyl-1-diethylaminocarbonyl-2-phthalimidomethylcyclopropane.

6. The process according to claim 1, wherein the concentration of the aqueous methylamine solution is from 10 to 25% by weight.

7. The process according to claim 1, wherein the amount of methylamine is 4 to 20 gram equivalent per one gram equivalent of (Z)-1-phenyl-1-diethylaminocarbonyl-2-phthalimidomethyl cyclopropane.

8. The process according to claim 1, wherein the organic solvent consists essentially of toluene.

\* \* \* \* \*